United States Patent
Zala et al.

(10) Patent No.: US 12,194,153 B2
(45) Date of Patent: *Jan. 14, 2025

(54) AMORPHOUS DISPERSION OF 4-METHYL-3-QUINOLIN-3-YLETHYNYL-BENZOIC ACID N'-(2-CHLORO-6-METHYL-BENZOYL) HYDRAZIDE

(71) Applicant: SUN PHARMA ADVANCED RESEARCH COMPANY LIMITED, Maharashtra (IN)

(72) Inventors: Yashoraj Zala, Maharashtra (IN); Bramhanand Hanamannavar, Maharashtra (IN); Nitin Dharmadhikari, Maharashtra (IN)

(73) Assignee: SUN PHARMA ADVANCED RESEARCH COMPANY LIMITED, Maharashtra (IN)

( * ) Notice: Subject to any disclaimer, the term of this patent is extended or adjusted under 35 U.S.C. 154(b) by 88 days.

This patent is subject to a terminal disclaimer.

(21) Appl. No.: 17/319,583

(22) Filed: May 13, 2021

(65) Prior Publication Data

US 2021/0267906 A1    Sep. 2, 2021

Related U.S. Application Data

(63) Continuation of application No. 16/494,543, filed as application No. PCT/IN2018/050146 on Mar. 15, 2018, now Pat. No. 11,351,123.

(30) Foreign Application Priority Data

Mar. 15, 2017 (IN) .............................. 201721005414

(51) Int. Cl.
*A61K 9/48* (2006.01)
*A61K 9/00* (2006.01)
(Continued)

(52) U.S. Cl.
CPC .......... *A61K 9/4866* (2013.01); *A61K 9/0053* (2013.01); *A61K 9/146* (2013.01);
(Continued)

(58) Field of Classification Search
None
See application file for complete search history.

(56) References Cited

U.S. PATENT DOCUMENTS 9,024,021 B2    5/2015    Sengupta et al.
11,351,123 B2   6/2022    Zala et al.

FOREIGN PATENT DOCUMENTS

CN    103435595 A    12/2013
CN    103502217 A    1/2014
(Continued)

OTHER PUBLICATIONS

Jan. 11, 2022, Japanese Office Action issued for related JP application No. 2019-550727.
(Continued)

*Primary Examiner* — Kyung S Chang
(74) *Attorney, Agent, or Firm* — Paratus Law Group, PLLC (57) ABSTRACT

An oral solid dosage form comprising a mixture of compound of formula I and a fusible polymeric carrier; and optionally pharmaceutically acceptable excipients, wherein the mixture is an amorphous dispersion.

22 Claims, 7 Drawing Sheets

(51) Int. Cl.
- *A61K 9/14* (2006.01)
- *A61K 31/47* (2006.01)
- *A61K 47/32* (2006.01)
- *A61K 47/34* (2017.01)
- *C07D 215/12* (2006.01)

(52) U.S. Cl.
CPC .............. *A61K 31/47* (2013.01); *A61K 47/32* (2013.01); *A61K 47/34* (2013.01); *C07D 215/12* (2013.01)

(56) References Cited

FOREIGN PATENT DOCUMENTS

| | | |
|---|---|---|
| CN | 105744847 A | 7/2016 |
| EP | 3596050 A4 | 1/2021 |
| JP | 2010-509289 A | 3/2010 |
| JP | 2014-510037 A | 4/2014 |
| JP | 2015-503613 A | 2/2015 |
| JP | 2014-510037 A5 | 3/2015 |
| JP | 2015-503613 A5 | 2/2016 |
| WO | WO 2007/075869 A2 | 7/2007 |
| WO | WO 2007/133560 A2 | 11/2007 |
| WO | WO 2012/098416 A1 | 7/2012 |
| WO | WO 2015/071394 A1 | 5/2015 |
| WO | WO 2015/128298 A1 | 9/2015 |
| WO | WO 2016/021707 A1 | 2/2016 |
| WO | WO-2016016665 A1 * | 2/2016 ........... A61K 31/495 |
| WO | WO-2016090240 A1 * | 6/2016 ........... A61K 31/519 |
| WO | WO 2018/167802 A1 | 9/2018 |

OTHER PUBLICATIONS

Herbrink et al., Inherent formulation issues of kinase inhibitors, Journal of Controlled Release, Aug. 28, 2016, pp. 118-127, Elsevier.
Hardung et al., Combining HME & solubilization: Soluplus®—The solid solution, Drug Delivery Technology, Apr. 2010, pp. 20, 21-27.
Linn et al., Soluplus® as an effective absorption enhancer of poorly soluble drugs in vitro and in vivo, European Journal of Pharmaceutical Sciences, 2012, pp. 336-343, Elsevier.
Apr. 27, 2021, Australia Examination Report issued for corresponding AU application No. 2018235446.
International Search Report and Written Opinion issued on May 25, 2018 for PCT Application No. PCT/IN2018/050146.
Oo et al., "Effects of Different Formulation Methods on Drug Crystallinity, Drug-Carrier Interaction, and Ex Vivo Permeation of a Ternary Solid Dispersion Containing Nisoldipine," Journal of Pharmaceutical Innovation, Dec. 12, 2019, pp. 1-12.
Jun. 22, 2021, Russian Office Action issued for related RU application No. 2019132068/04(063180).
Belikov V.G., Pharmaceutical Chemistry, textbook, MEDpress-inform, 2007, pp. 27-29, Moscow (see RU Office Action Translation above for a concise description of relevance).
Kondratieva T.S. et al., Technology of dosage forms: Textbook in 2 volumes, 1991, pp. 39-41, vol. 1 (see RU Office Action Translation above for a concise description of relevance).
Industrial Drug Technology, 2002, p. 11, vol. 2, Publishing house of NFAU MTK-Kniga (see RU Office Action Translation above for a concise description of relevance).
Van Den Mooter, The use of amorphous solid dispersions: a formulation strategy to overcome poor solubility and dissolution rate, Drug Discovery Today: Technologies, 2012, pp. e79-e85, vol. 9, No. 2.
I.I. Krosnyuk et al., Pharmaceutical Engineering: Dosage Form Technology: textbook for students of higher educational institutions 2nd ed., pp. 297-299, The Academia Publishing Center (see RU Office Action Translation above for a concise description of relevance).
Industrial Drug Technology, 2002, p. 10, vol. 2, Publishing house of NFAU MTK-Kniga (see RU Office Action Translation above for a concise description of relevance).
Sep. 1, 2022, Chinese Office Action issued for related CN Application No. 201880018595.X.
Wang Lu et al., Advances in the Application of Soluplus® Copolymer in new Drug Dosage Forms and New Techniques, Chinese Pharmacy, 2016, pp. 2703-2707, Vo. 27, No. 19.
Dec. 22, 2021, Russian Office Action issued for related RU application No. 2019132068/04.
Kondratyeva, The Technology of Dosage Forms: Textbook in 2 volumes, 1991, pp. 39-41, vol. 1, M.: Medicine (see Translation of Russian Office Action for concise relevance).
Krosnyuk et al., Pharmaceutical Technology: Dosage Form Technology: Student Textbook for Higher Educational Institutions., 2006, p. 297-299, Edition 2, reprint, M.: Publishing Center Akademiya (see Translation of Russian Office Action for concise relevance).
Zhulenko et al., Pharmacology, 2008, p. 34-35, M.: ColosS (see Translation of Russian Office Action for concise relevance).
Kharkevich, Pharmacology, 2010, p. 73-74, Ed. 10, M.: GEOTAR-Media (see Translation of Russian Office Action for concise relevance).
Chueshov et al., Industrial Technology of Drugs, 2002, p. 11, vol. 2, Kharkov, Publishing House NFAU MTK-Kniga (see Translation of Russian Office Action for concise relevance).
Oct. 23, 2023, Canadian Office Action issued for related CA Application No. 3,056,348.

* cited by examiner

AMORPHOUS DISPERSION OF 4-METHYL-3-QUINOLIN-3-YLETHYNYL-BENZOIC ACID N'-(2-CHLORO-6-METHYL-BENZOYL) HYDRAZIDE

CROSS REFERENCE TO PRIOR APPLICATION

This application is a continuation of U.S. patent application Ser. No. 16/494,543 (filed on Sep. 16, 2019), which is a National Stage Patent Application of PCT International Patent Application No. PCT/IN2018/050146 (filed on Mar. 15, 2018) under 35 U.S.C. § 371, which claims priority to Indian Patent Application No. 201721005414 (filed on Mar. 15, 2017), which are all hereby incorporated by reference in their entirety.

FIELD OF INVENTION

The present invention relates to an amorphous dispersion of 4-Methyl-3-quinolin-3-ylethynyl-benzoic acid N'-(2-chloro-6-methyl-benzoyl)hydrazide and an oral solid dosage form comprising the amorphous dispersion.

BACKGROUND OF THE INVENTION

U.S. Pat. No. 9,024,021 discloses a compound of Formula I (4-Methyl-3-quinolin-3-ylethynyl-benzoic acid N'-(2-chloro-6-methyl-benzoyl)hydrazide).

Formula I

Compound of Formula I is a potent inhibitor of Abl tyrosine kinase. Conventional oral solid dosage forms of compound of Formula I failed to provide adequate bioavailability. There remains a need to provide the compound of formula I in a bioavailable form. There is a need for an oral solid dosage form of the compound of formula I that has adequate bioavailability and stability.

SUMMARY OF THE INVENTION

The present inventors have discovered novel amorphous dispersion of compound of Formula I in a fusible polymeric carrier and oral solid dosage form comprising the amorphous dispersion. The oral solid dosage form of the amorphous dispersion provides enhanced bioavailability as well as stability.

In a preferred embodiment, the present invention provides an oral solid dosage form comprising a mixture of a compound of formula I Formula I and a fusible polymeric carrier, wherein the mixture is an amorphous dispersion. The oral, solid dosage form optionally comprises of pharmaceutically acceptable excipients. The amorphous dispersion in the oral solid dosage form of the invention is physically and chemically stable during melt processing and the oral, solid dosage form remains stable on storage. Particularly, when the oral solid dosage form is stored at room temperature for 24 months, each of the degradation impurity such as stage V impurity and N-oxide impurity is less than 0.2% by weight of the compound of formula I and the total impurity, which is a sum of known and unknown impurities, is less than 2% by weight of the compound of formula I. Further, the compound of formula I remained in an amorphous state during the period of storage.

DESCRIPTION OF THE PRESENT INVENTION

Figure 3:
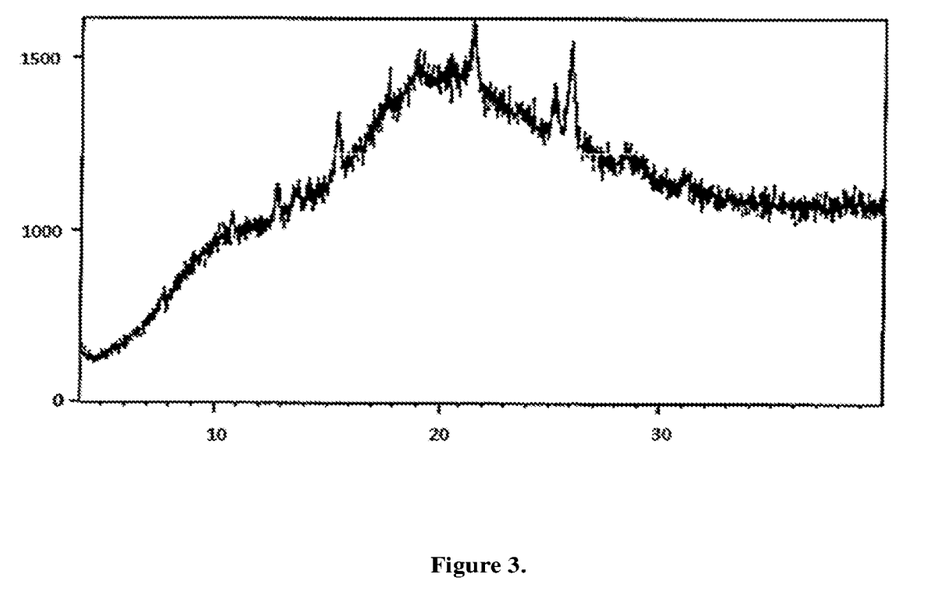
FIG. 3. X-ray diffraction spectrum of a physical mixture of fusible polymeric carrier, namely, polyvinyl caprolactam-polyvinyl acetate-polyethylene glycol copolymer and compound of formula I. The graph exhibits X-ray diffraction peaks characteristic of the crystalline form of compound of formula 1.
Figure 4:
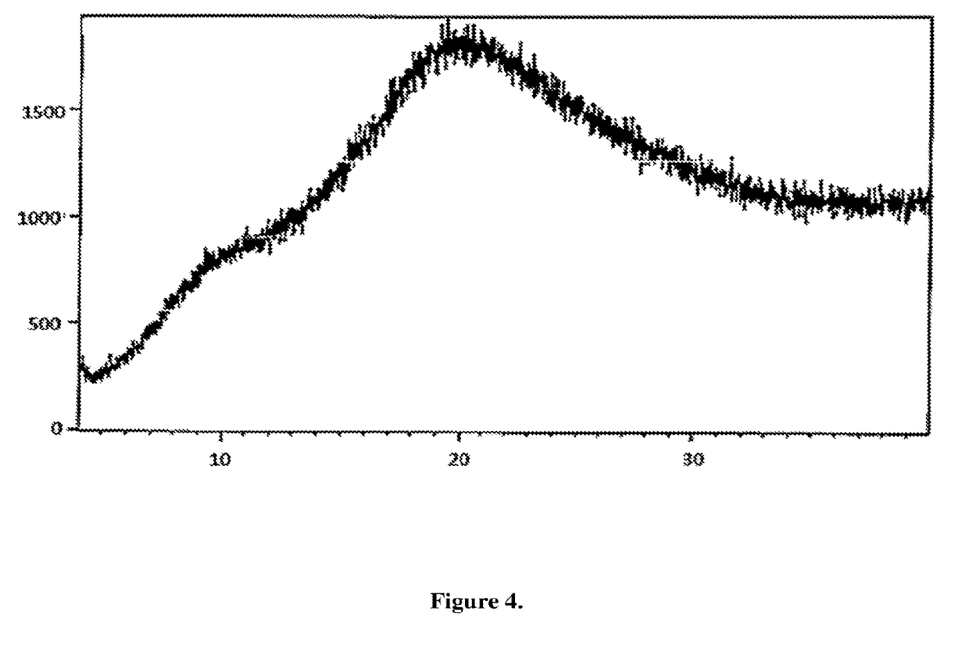
FIG. 4. X-ray diffraction spectrum of amorphous dispersion of compound of formula I in a fusible polymeric carrier, namely, polyvinyl caprolactam-polyvinyl acetate-polyethylene glycol copolymer. The graph did not exhibit any X-ray diffraction peak characteristic of the crystalline form of compound of formula I.

The present invention provides an oral, solid dosage form comprising a mixture of compound of formula I Formula I and a fusible polymeric carrier; and
optionally pharmaceutically acceptable excipients, wherein the mixture is an amorphous dispersion.

of formula I or the dispersion that does not exhibit the melting peak of the crystalline compound of formula I in a Differential scanning calorimetry analysis (DSC). The XRD spectrum of amorphous dispersion of compound of formula I in fusible polymeric carrier is provided in FIG. 4 which shows absence of X-ray diffraction peaks characteristic of crystalline form of compound of formula I. In contrast, the XRD of the physical mixture of crystalline compound of formula I and fusible polymeric carrier, exhibited X-Ray Diffraction peaks characteristic of crystalline form of the compound of Formula I, as depicted in FIG. 3. FIG. 4 clearly shows the amorphous state of compound of formula I in a fusible polymeric carrier.

The term 'stable' or 'stability' as used herein means that the dosage form is physically and chemically stable. The 'chemically stable' means that the oral solid dosage form when stored at room temperature for 24 months, each of the degradation impurity such as stage V impurity and N-oxide impurity is less than 0.2% by weight of the compound of formula I and the total impurity, which is a sum of known and unknown impurities, is less than 2% by weight of the compound of formula I. The known degradation impurities of compound of formula I are named as N-oxide impurity and stage V impurity.

| Name of the impurity | Chemical Name | Chemical Structure |
|---|---|---|
| N-oxide impurity | 3-(1-Hydroxy-quinolin-3-ylethynyl)-4-methyl-benzoic acid N'-(2-chloro-6-methyl-benzoyl)hydrazide | |
| Stage V impurity | 4-Methyl-3-quinolin-3-ylethynyl-benzoic acid | |

'Physically stable' means that when the oral solid dosage form of the present invention is stored at room temperature, the compound of formula I remain in an amorphous state.

Figure 1:
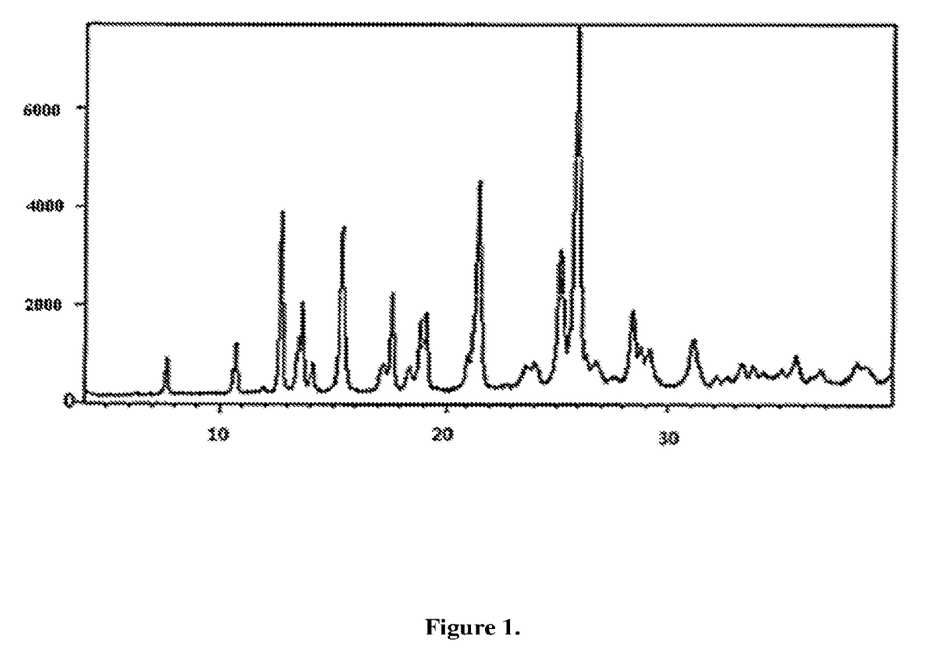
FIG. 1. X-ray diffraction spectrum exhibits peaks characteristic of crystalline form of compound of formula I.
Figure 2:
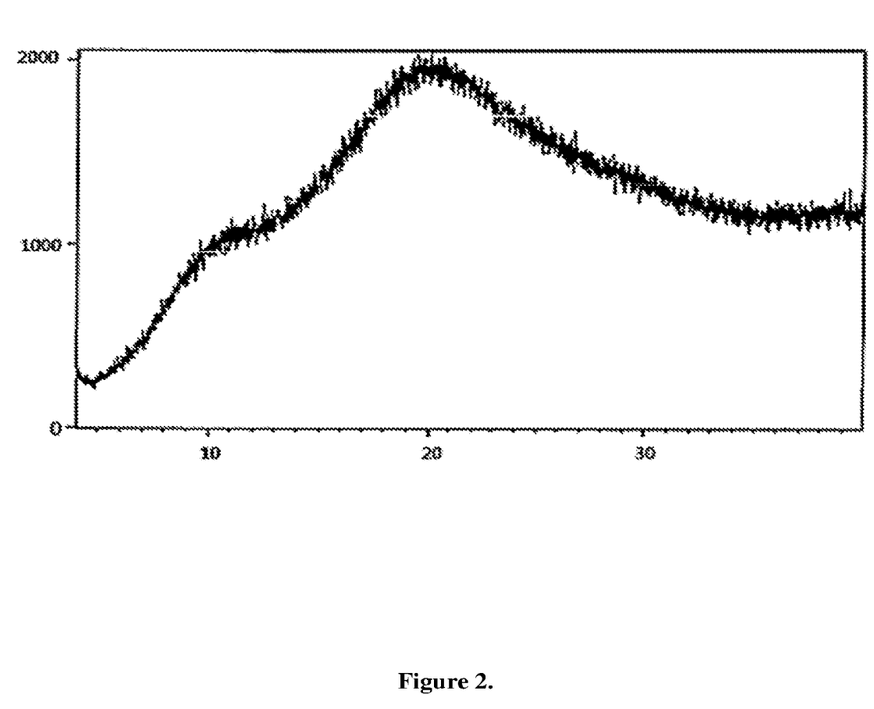
FIG. 2. X-ray diffraction spectrum of a fusible polymeric carrier, namely, polyvinyl caprolactam-polyvinyl acetate-polyethylene glycol copolymer.

According to the present invention, the mixture of compound of Formula I and fusible polymeric carrier is an amorphous dispersion. The amorphous nature of the dispersion of compound of formula I may be determined by techniques known in the art. In one instance, the amorphous nature is determined by recording the X-ray Powder Diffraction (XRD) or by Differential scanning calorimetry analysis (DSC). The XRD spectrum of compound of formula I showing the X-ray diffraction peaks characteristic of the crystalline form is provided in FIG. 1 and the DSC is provided in FIG. 5. The XRD spectrum of fusible polymeric carrier namely, polyvinyl caprolactam-polyvinyl acetate-polyethylene glycol copolymer is provided in FIG. 2.

The term 'amorphous dispersion' as used herein means a solid dispersion of mixture of compound of formula I in a fusible polymeric carrier that does not exhibit X-ray diffraction peaks characteristic of the crystalline form of compound

The fusible polymeric carrier used in the amorphous dispersion of the oral solid dosage form of the present invention may be any fusible polymeric carrier that forms an amorphous dispersion with compound of formula I when the mixture of the fusible polymeric carrier and compound of formula I is processed by melt processing. According to one specific embodiment, the fusible polymeric carrier present in the amorphous dispersion of the present invention, is amphiphilic in nature and is soluble in aqueous medium as well as organic solvents such as alcohols, acetone, dimethylformamide and the like. Examples of such polymers include block copolymers of ethylene oxide and propylene oxide, polyvinyl caprolactam-polyvinyl acetate-polyethylene glycol copolymer, vinylpyrrolidone-vinyl acetate copolymer, polyethylene glycols having molecular weight of 1000 or more which are solid at room temperature, or mixtures thereof. According to an embodiment, the fusible polymer is polyethylene glycol having average molecular weight more than 1000 such as 1000, 2000, 1450, 1540, 2000, 3000, 3350, 4000, 4600, 8000 and mixtures thereof and the like. In one preferred embodiment, the fusible polymeric carrier is polyvinyl caprolactam-polyvinyl acetate-polyethylene glycol graft copolymer. It is soluble in water, acetone, methanol, ethanol and dimethylformamide; and is available in an average molecular weight in the range of 1,000 g/mol to about 5,000,000 g/mol. The polymer does not show any chemical degradation when melt processed. Preferably, the molecular weight is in the range from about 10,000 g/mol to about 500,000 g/mol. In one preferred embodiment the molecular weight is in the range from about 90,000 g/mol to about 140,000 g/mol. In yet another preferred embodiment, polyvinyl caprolactam-polyvinyl acetate-polyethylene glycol copolymer has a molecular weight in the range of from about 140,000 g/mol to 500,000 g/mol According to one preferred embodiment of the invention, the amorphous dispersion is free of any other excipients. According to other embodiment, additional excipients may be present in the amorphous dispersion in limited amounts. The fusible polymeric carrier may be first selected by melt processing a mixture of compound of formula I and the fusible polymeric carrier and performing a suitable test such as X-Ray Diffraction or Differential Scanning Calorimetry to find that amorphous dispersion is formed. Those polymers when subjected to heating near the melting point of the compound of formula I substantially degrade or decompose are not within the scope of the term 'fusible polymeric carrier'. Examples of such polymers include, but are not limited to, cellulose derivatives, such as for example, hydroxypropyl cellulose, hydroxypropyl methyl cellulose, hydroxypropyl methyl cellulose acetate succinate, hydroxypropyl methyl cellulose phthalate, acrylate polymers such as poly (methacrylic acid co-ethyl acrylate 1:1), poly (butylmethylacrylate co-dimethylaminoethyl methacrylate co-methyl methacrylate (1:2:1) and similar such polymers.

In one preferred embodiment, the amorphous dispersion contains compound of Formula I in the range from 0.1 to 30% by weight of the amorphous dispersion, for example 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30% by weight of the amorphous dispersion. The fusible polymeric carrier is present in the range from 10 to 99% by weight of the amorphous dispersion, for example 10, 20, 30, 40, 50, 60, 70, 80, 90, 95, 96, 97, 98, or 99% by weight of the amorphous dispersion. In one particular embodiment, the weight ratio of fusible polymeric carrier to compound of formula I is present in the range from 1 to 20, for example 1, 2, 3, 4, 5, 6, 7, 8, 9, 10, 11, 12, 13 and so on. Preferably, the weight ratio of fusible polymeric carrier to compound of formula I is present in the range from 4:1 to 14:1. More preferably, the weight ratio of fusible polymeric carrier to compound of formula I is about 7:1.

According to a preferred embodiment, the amorphous dispersion of fusible polymeric carrier and compound of formula I Formula I is prepared by a process of melting the mixture of the two components i.e. compound of Formula I and fusible polymeric carrier by a suitable technique such as hot melt extrusion.

The preferred methods of preparing the amorphous dispersion may be by melt processing, however it is also possible and within the scope of the present invention to prepare the amorphous dispersion by other methods as described herein. Melt process generally involves mixing the compound of formula I with a fusible polymeric carrier and heating to form a molten solution. According to another embodiment, the mixture of the fusible polymeric carrier and the compound of formula I may be heated to a temperature near melting point of the fusible polymeric carrier while mixing or agitating to dissolve the compound of formula I in the molten fusible polymeric carrier. The hot melt solution is then cooled to obtain the amorphous dispersion. In another embodiment, the mixture of the compound of formula I and the fusible polymeric carrier is heated to a temperature near the melting points of the compound of formula I which has a melting point of 246±2° C. In another more particularly preferred embodiment, the amorphous dispersion may be obtained by hot melt extrusion. The fusible polymeric carrier is mixed with the therapeutically effective amount of compound of formula I and subjected to hot melt extrusion. The hot melt extrusion may be carried out by subjecting the mixture to gradual increase in temperature, starting from 100° C. to 300° C., followed by cooling at ambient temperature. According to the embodiments where the mixture is melted, the molten solution obtained may be cooled and solidified, and the solid mass is crushed and pulverized in a suitable mill to obtain the amorphous dispersion in the form of granules or powder.

According to another embodiment, the amorphous dispersion of the compound of formula I may also be prepared by dissolving the compound of formula I and fusible polymeric carrier in a common solvent and evaporating it until a clear, solvent free film is formed. Other method of preparation of amorphous dispersion is by dissolving the compound of formula 1 in a suitable liquid solvent and then incorporating the solution directly into the melt of a fusible polymeric carrier which is then evaporated until a clear, solvent free film is formed. The film may be further pulverized to suitable size by conventional techniques. The amorphous dispersion obtained by any of the methods described above, is clear and transparent in appearance. The amorphous dispersion of the present invention is generally pulverized. The pulverization of the amorphous dispersion may be done by any conventional technique. The pulverized amorphous dispersion is free flowing and has acceptable compressibility. The bulk density of the pulverized amorphous dispersion of present invention is less than 0.7 g/ml, preferably 0.4, 0.5, 0.6 g/ml. In one specific embodiment, the bulk density is 0.52, 0.53, 0.54, 0.55, 0.56 g/ml.

In one embodiment, the amorphous dispersion is obtained in the solid form. The mass is pulverized using known techniques to obtain powder. The particle size of the pulverized amorphous dispersion may be less than 1000 microns, preferably, less than 750 microns, most preferably, less than 500 microns. In one specific embodiment, the particle size is in the range of about 75 microns to 425 microns. In one preferred embodiment, the size of the pulverized amorphous dispersion is below 600 microns, preferably below 425 microns and more preferably below 180 microns. Preferably, the size of the particles is below 425 microns. According to an embodiment, about 100% of the particles of the pulverized amorphous dispersion are of size less than 425 microns. According to another embodiment, about 85% of the particles are of size less than 250 microns. According to one another embodiment, about 65% of the particles are of size less than 180 microns. According to one another embodiment, about 45% of the particles are of size less than 150 microns. According to yet another embodiment, about 15% of the particles are of size less than 75 microns.

In one specific embodiment, the present invention provides an oral, solid dosage form comprising a mixture of compound of formula I Formula I and a fusible polymeric carrier; and optionally pharmaceutically acceptable excipients, wherein the mixture is an amorphous dispersion, further wherein the fusible polymeric carrier is polyvinyl caprolactam-polyvinyl acetate-polyethylene glycol graft co-polymer. In a preferred embodiment, the weight ratio of the fusible polymeric carrier to compound of formula I is about 7:1. Generally, the amorphous dispersion is in the micronized form. The amorphous dispersion when in the pulverized form, all the particles have size less than 750 microns, preferably less than 500 microns.

In one another specific embodiment, the present invention provides an oral, solid dosage form comprising a mixture of compound of formula I Formula I and a fusible polymeric carrier; and optionally pharmaceutically acceptable excipients, wherein the mixture is an amorphous dispersion, further wherein the fusible polymeric carrier may be polyvinyl caprolactam-polyvinyl acetate-polyethylene glycol graft co-polymer. In preferred embodiment, the weight ratio of the fusible polymeric carrier to compound of formula I is about 7:1. Generally, the amorphous dispersion is in the micronized form. The amorphous dispersion when in the pulverized form, all the particles have size less than 750 microns, preferably less than 500 microns. It may be noted that the fusible polymeric carrier is not a polymer which melts with substantial degradation or decomposition when heated near the melting point of compound of formula I. The examples of polymers that degrade or decompose substantially when subjected to melting or heating at the temperature near the melting point of compound of formula I, include, but are not limited to, cellulose derivatives, such as for example, hydroxypropyl cellulose, hydroxypropyl methyl cellulose, hydroxypropyl methyl cellulose acetate succinate, hydroxypropyl methyl cellulose phthalate, acrylate polymers such as poly (methacrylic acid co-ethyl acrylate 1:1), poly (butylmethylacrylate co-dimethylamino ethyl methacrylate co-methyl methacrylate (1:2:1) and similar such polymers.

In yet another specific embodiment, the present invention provides an oral, solid dosage form comprising a mixture consisting essentially of compound of formula I Formula I and a fusible polymeric carrier; and optionally pharmaceutically acceptable excipients, wherein the mixture is an amorphous dispersion, further wherein the fusible polymeric carrier may be polyvinyl caprolactam-polyvinyl acetate-polyethylene glycol graft co-polymer. In this embodiment, the amorphous dispersion which is a mixture of compound of formula I and fusible polymeric carrier contains only the fusible polymeric carrier and is free of any other excipient or polymer which was found to degrade or decompose substantially when subjected to heating near the melting point of the compound of formula I. Such polymers or excipients include, but are not limited to, cellulose derivatives such as for example, hydroxypropyl cellulose, hydroxypropyl methyl cellulose, hydroxypropyl methyl cellulose acetate succinate, hydroxypropyl methyl cellulose phthalate, acrylate polymers such as poly (methacrylic acid co-ethyl acrylate 1:1), poly (butylmethylacrylate co-dimethylamino ethyl methacrylate co-methyl methacrylate (1:2:1) and like.

In preferred embodiment, the weight ratio of the fusible polymeric carrier to compound of formula I is about 7:1. Generally, the amorphous dispersion is in the micronized form. The amorphous dispersion when in the pulverized form, all the particles have size less than 750 microns, preferably less than 500 microns.

In one another specific embodiment, the present invention provides an oral, solid dosage form comprising a mixture consisting of compound of formula I

Formula I and a fusible polymeric carrier; and optionally pharmaceutically acceptable excipients, wherein the mixture is an amorphous dispersion, further wherein the fusible polymeric carrier may be polyvinyl caprolactam-polyvinyl acetate-polyethylene glycol graft copolymer. Alternatively, the amorphous dispersion is a mixture comprising compound of formula I Formula I and a fusible polymeric carrier wherein the mixture is substantially free of excipients which were found to degrade or decompose substantially when subjected to heating near the melting point of the compound of formula I.

The amorphous dispersion of the compound of Formula I and fusible polymeric carrier may be directly compressed into tablets or filled into a capsule, sachet or pouch. More preferably, the amorphous dispersion is converted into tablets or capsules using pharmaceutically acceptable excipients. Methods used include, conventional methods such as those where the amorphous dispersion is mixed with the pharmaceutically acceptable excipients and converted into tablets by direct compression or converted into capsules by filling the mixture into capsules or alternatively converted into granules by wet granulation or dry granulation and the granules filled into capsules or compressed into tablets. The oral solid dosage form of the present invention may be obtained by mixing the amorphous dispersion obtained by any one of the above methods with other conventional excipients like disinegrants, wicking agents, lubricams, surfactants, buffers, diluents and converting the mixture to an oral solid dosage form, for example it may be filled into hard gelatin capsule, pouches, sachets, or compressed into tablets. According to an embodiment, the oral solid dosage form is a hard gelatin capsule filled with the milled amorphous dispersion comprising compound of formula I and polyvinyl caprolactarn-polyvinyl acetate-polyethylene glycol copolymer as the fusible polymeric carrier. According to another embodiment, the oral solid dosage form is a compressed tablet comprising the milled amorphous dispersion of compound of formula I and polyvinyl caprolactam-polyvinyl acetate-polyethylene glycol copolymer as the fusible polymeric carrier and other conventional pharmaceutical excipients. In one preferred embodiment, these filled hard gelatin capsules or tablets are packed in closed containers with a desiccant and are stored at 25° C. and 60% relative humidity.

The oral solid dosage form of the present invention is physically stable. That is the compound of formula I remains in the amorphous state and does not get converted into crystalline state during its shelf life when stored at ambient conditions. The amorphous nature of compound of Formula I in the oral solid dosage form may be determined by either X-ray diffraction or differential scanning calorimetric analysis (DSC). The XRD spectrum of crystalline form of compound of formula I shows characteristic diffraction peaks and DSC shows a characteristic melting peak at about 246±2° C. The DSC of the oral solid dosage form of the present invention does not show melting peak at about 246±2° C. characteristic of crystalline compound of formula I at initial time point as well as upon storage at 40° C. and 75% relative humidity for 6 months. In order to confirm the amorphous nature, the XRD or DSC of the placebo excipient blend is also recorded. The absence of characteristic, diffraction peaks in the XRD spectrum, or melting peak at about 246±2° C. in the DSC spectrum, which are characteristic of crystalline compound of formula I proves that the compound of formula I is in the amorphous state in the oral solid dosage form of the present invention upon storage.

The oral solid dosage form of the present invention is also chemically stable. This means that, each of the degradation impurity such as stage V impurity and N-oxide impurity is less than 0.2% by weight of the compound of formula I. Also the total impurity, which is sum of known and unknown impurities, is less than 2% by weight of the compound of formula I. In a preferred embodiments, each of the degradation impurity such as stage V impurity and N-oxide impurity is less than 0.2%, preferably in the range of 0.001 to 0.15%, preferably, 0.01 to 0.1% by weight of the compound of formula 1. Also, the total impurity is less than 2%, preferably, less than 0.001 to 1.5% or 0.01 to 1% by weight of the compound of Formula I.

Further, the amorphous dispersion provided an improved oral bioavailability in that the rate and extent of absorption of compound of formula I was significantly enhanced as compared to the plasma levels when the crystalline form of compound of formula I in a vehicle was administered to dogs. The enhancement in bioavailability was significant i.e. it was found to be in magnitude of about 3, 5, 10, 20, 30, 40, 50 times higher as compared to the bioavailability obtained when the crystalline form of compound of formula I in a vehicle was administered orally. Thus, the oral, solid dosage of the present invention was not only stable both chemically and physically, but was also made orally bioavailable.

The pharmaceutically acceptable excipients are the ones that are used conventionally and are known in the art. These include diluents, disintegrants, wicking agents and surfactants. Examples of disintegrating agents used include, but are not limited to, natural starch, pregelatinized starch, sodium starch glycolate, microcrystalline cellulose, methylcellulose, croscarmellose, cross-linked cellulose, cross-linked sodium carboxymethylcellulose, cross-linked carboxymethylcellulose, cross-linked croscarmellose, cross-linked starch, sodium starch glycolate, crospovidone, cross-linked polyvinylpyrrolidone, alginic acid, sodium alginate, magnesium aluminum silicate, agar, guar, locust bean, karaya, pectin, tragacanth, sodium starch glycolate, bentonite, cation-exchange resin, sodium lauryl sulfate, or in combination thereof. In an embodiment, disintegrant used in oral solid dosage form is present in an amount ranging from about 0.1% to 10% of the total weight of the oral solid dosage form. In an embodiment, surfactant used in oral solid dosage form is present in an amount ranging from about 1% to 10% of the total weight of the oral solid dosage form.

Lubricants or glidants used in the oral solid dosage form are selected from group consisting of, but are not limited to, silicon dioxide, stearic acid, calcium hydroxide, talc, corn starch, sodium stearyl fumarate, alkali-metal and alkaline earth metal salts, stearic acid, sodium stearates, magnesium stearate, zinc stearate, waxes, boric acid, sodium benzoate, sodium acetate, sodium chloride, leucine, polyethylene glycol, methoxypolyethylene glycol, polyethylene glycol 4000, polyethylene glycol 5000, polyethylene glycol 6000, propylene glycol, sodium oleate, glyceryl behenate, glyceryl palmitostearate, glyceryl benzoate, magnesium or sodium lauryl sulfate, and the like. The glidant used in oral solid dosage form is present in an amount ranging from about 0.1% to 3% of the total weight of the oral solid dosage form. Diluents used in oral solid dosage form are selected from the group consisting of, but are not limited to lactose, starch, mannitol, sorbitol, dextrose, microcrystalline cellulose, dibasic calcium phosphate, dicalcium phosphate dehydrate, tricalcium phosphate, calcium phosphate, anhydrous lactose, spray-dried lactose, pregelatinized starch, compressible sugar, mannitol, hydroxypropylmethylcellulose, hydroxypropylmethylcellulose acetate stearate, sucrose-based diluents, sugar, monobasic calcium sulfate monohydrate, calcium sulfate dehydrate, calcium lactate trihydrate, dextrates, hydrolyzed cereal solids, amylose, powdered cellulose, calcium carbonate, glycine, kaolin, mannitol, sodium chloride, inositol, bentonitc, silicified microcrystalline cellulose and combination thereof. The diluent used in oral solid dosage form is present in an amount ranging from about 1% to 90% of the total weight of the oral solid dosage form.

The invention will now be further described by the following examples, which are illustrative rather than limiting.

Examples I and II

TABLE 1

Composition of the amorphous dispersion

| Ingredients | % by weight | |
|---|---|---|
| | Example I | Example II |
| Compound of Formula I | 12 | 13.3 |
| Polyvinyl caprolactum-polyvinyl acetate-polyethylene glycol co-polymer | 88 | 43.33 |
| Polyethylene glycol | — | 43.33 |

The specified amounts of compound of formula I and polyvinyl caprolactum-polyvinyl acetate-polyethylene glycol co-polymer were sifted and mixed in a blender (Example II additionally included polyethylene glycol 4000). The resulting blend was then charged to a hot melt extruder gradually to a higher temperature (100° C. to 230° C.) yielding the melt extrudates. The extrudates were then milled in a comminuting mill fitted with 4.00 mm screen at 2000-2400 RPM which was sifted through ASTM #40 and loaded in a blender. The final content was collected in a suitable container and was subjected to sieve analysis. It was observed that about 100% of the particles were less than 425 microns. The milled particles were of the size in the range of about 75 microns to 425 microns. Further, about 85% of the particles were of size less than 250 microns; about 65% of the particles were of size less than 180 microns; about 45% of the particles were of size less than 150 microns; and about 15% of the particles were of size less than 75 microns. The milled particles of amorphous dispersion had bulk density in the range of about 0.52 to 0.56 g/ml and had acceptable flow characteristics. The extrudates were also subjected to X-Ray diffraction. It was observed that the X-Ray diffraction of melt extrudates of Example I (FIG. 4) did not exhibit any peaks characteristic of crystalline form of compound of formula I, confirming its amorphous nature.

Example III

Suitable amount of amorphous dispersion of Example I and the crystalline form of compound of formula I suspended in a vehicle were administered orally to dogs.

Blood samples were withdrawn at various time intervals and the plasma levels of compound of formula I were recorded. The $C_{max}$, $AUC_{0\ to\ t}$ and $AUC0\text{-}\infty,\ in\ in$ plasma are tabulated below.

TABLE 2

Bioavailability data

| Pharmacokinetic parameters | Compound of formula I in a vehicle | Amorphous dispersion of Example I |
|---|---|---|
| $C_{max}$ (ng/ml) | 282 | 2278 |
| $AUC_{0\ to\ t}$ (ng · hr/ml) | 1073 | 6412 |
| $AUC_{0\ to\ \infty}$ (ng · hr/ml) | 1187 | 7034 |

From the above table, it is evident that the oral administration of amorphous dispersion comprising compound of Formula I, showed significantly higher oral bioavailability ($C_{max}$, $AUC_{0\ to\ t}$, $AUC_{0to\ \infty}$) of compound of formula I as compared to test which did not include the compound of formula I as an amorphous dispersion with fusible polymeric carrier, namely polyvinyl caprolactam-polyvinyl acetate-polyethylene glycol co-polymer, but was simply dispersed in a vehicle. The oral bioavailability was increased to about six times when same amount of compound of formula I was orally administered.

Example IV

The amorphous dispersion of Example I was mixed with other conventional excipients like disintegrants, wicking agents, surfactants, lubricants, buffers, diluents and was filled into hard gelatin capsules. The oral solid dosage form in the form of filled capsules is given below:

TABLE 3

Oral solid dosage form as capsules filled with the amorphous dispersion

| Ingredients | % by weight of blend filled into capsule |
|---|---|
| Amorphous Dispersion of Example I | 78.43 |
| Silicon dioxide | 1.57 |
| Sodium lauryl sulfate | 2.55 |
| Crospovidone | 9.02 |
| Silicified microcrystalline cellulose | 8.43 |

Procedure: The milled extrudates of amorphous dispersion prepared in example I, silicon dioxide and sodium lauryl sulfate were sifted and loaded in a blender and mixed. Silicified microcrystalline cellulose and crospovidone each was sifted separately and were loaded in the blender containing the mixture of milled extrudates, silicon dioxide and sodium lauryl sulfate, and were blended. The blend was filled into hard gelatin capsules of appropriate size to the target fill weight which was filled into high density polyethylene bottles of appropriate capacity with desiccant and child resistant closures.

Example V

The capsules of Example IV were subjected to stability conditions at 25° C. and 60% relative humidity for 24 months and the impurities and related substances were measured. These capsules were also subjected to accelerated stability conditions at 40° C. and 75% relative humidity for 3 months. The impurities and related substances were measured before (initial) and after storage. The results are provided below in table 4.

TABLE 4

Stability data of oral solid dosage form of Example IV

| Related Substances/ degradation impurities | Initial | 40° C./75% Relative humidity for three months | 25° C./60% Relative humidity for 24 months |
|---|---|---|---|
| | % by weight of compound of formula I | | |
| Stage V Impurity | <0.020 | <0.020 | <0.020 |
| N-oxide Impurity | <0.039 | <0.039 | 0.082 |
| Highest unknown impurity | 0.138 | 0.157 | 0.142 |
| Total Impurities | 0.244 | 0.293 | 0.269 |

The stability study data showed that the degradation impurities like stage V impurity, N-oxide impurity, highest unknown impurity and total impurities were well within the acceptable limits. This demonstrated that the amorphous dispersion of compound of formula I in the oral solid dosage form was chemically stable.

Figure 5:
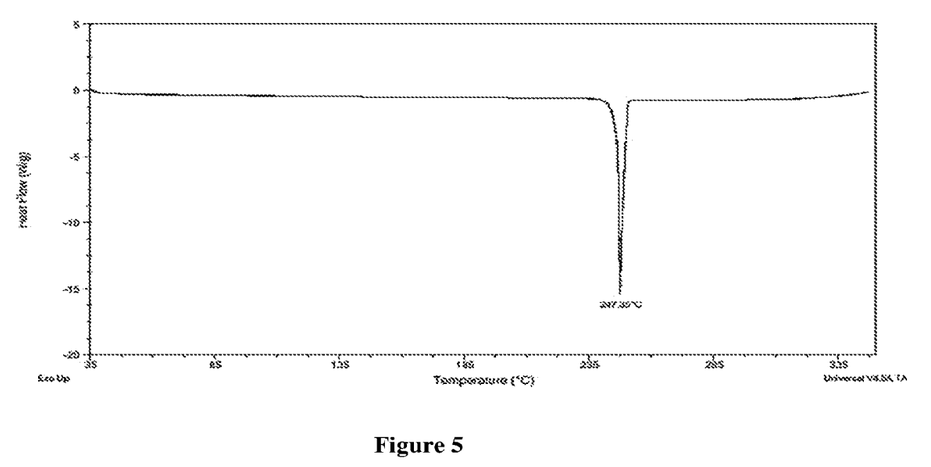
FIG. 5. Differential scanning calorimetry analysis (DSC) of compound of formula I in the crystalline form.
Figure 6:
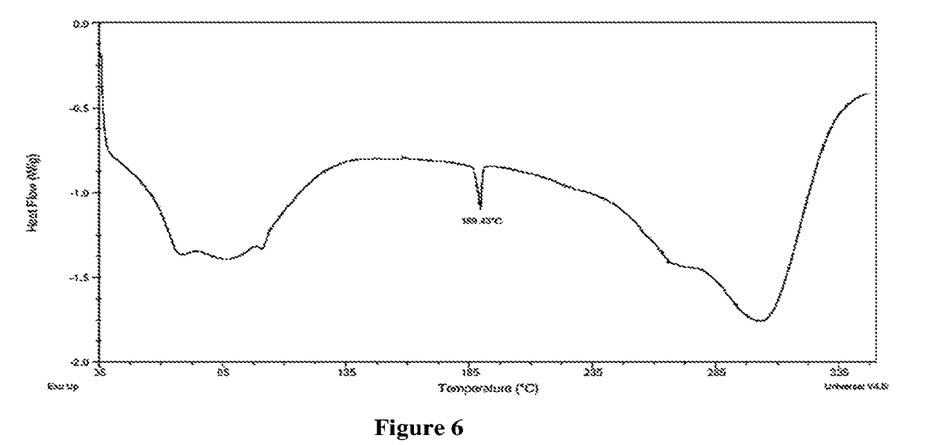
FIG. 6. Differential scanning calorimetry analysis (DSC) of the excipient blend of capsules of Example IV (placebo), in which the amorphous dispersion contains only the fusible polymeric carrier without the inclusion of compound of formula I.
Figure 7:
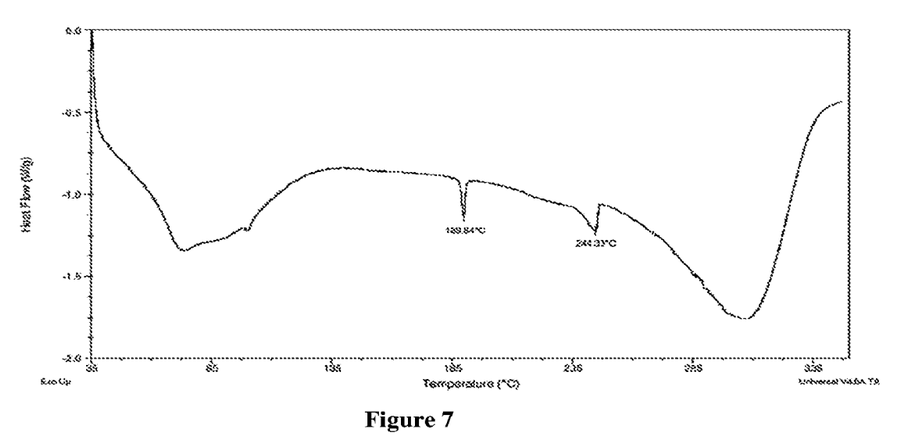
FIG. 7. Differential scanning calorimetry analysis (DSC) of the physical mixture of the compound of formula I, fusible polymeric carrier and other excipients of Example IV.
Figure 8:
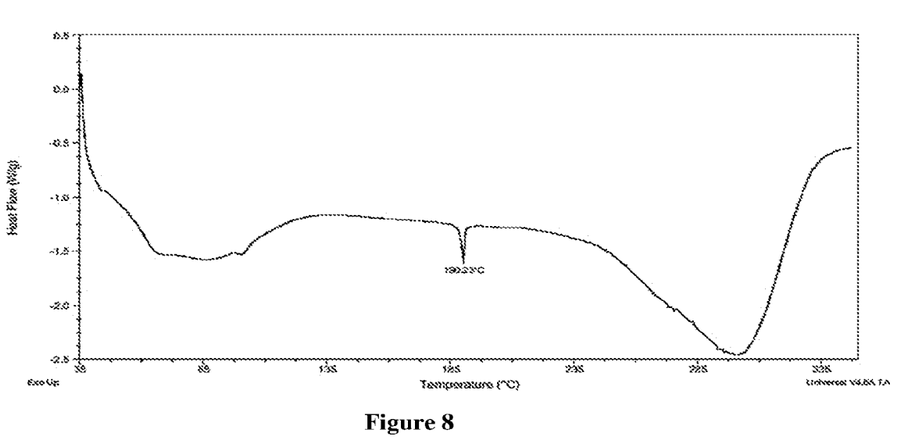
FIG. 8. Differential scanning calorimetry analysis (DSC) of the capsule fill of Example IV, at initial time point when the capsules are stored in closed container with desiccant at 40° C. and 75% relative humidity.
Figure 9:
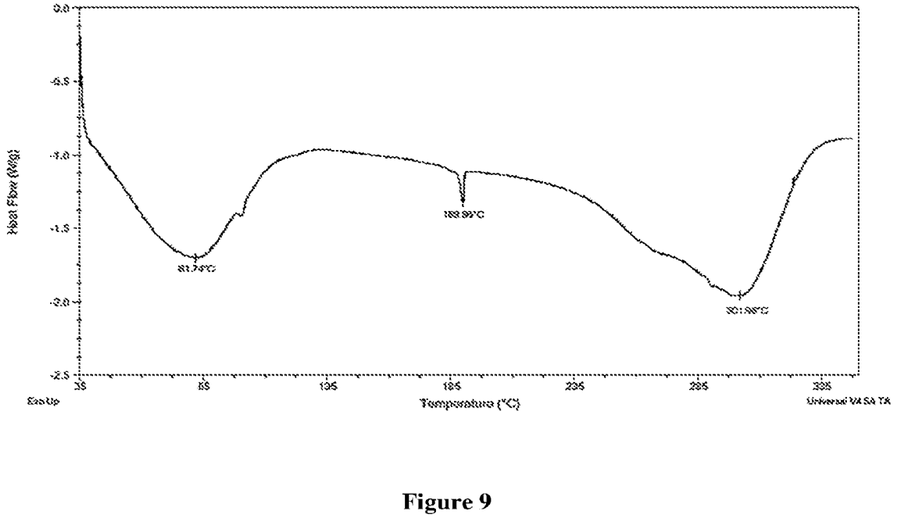
FIG. 9. Differential scanning calorimetry analysis (DSC) of the capsule fill of Example IV, on storage in closed container with desiccant at 40° C. and 75% relative humidity for a period of 6 months.

The blend of capsule of Example IV stored at 40° C. and 75% relative humidity for 6 months in closed container with a desiccant was subjected to DSC analysis. Also the placebo excipients blend of capsule without compound of formula I was subjected to DSC analysis to rule out the interference of the excipients or the fusible polymeric carrier (FIG. 6). The DSC of crystalline form of compound of formula I is presented in FIG. 5 showing sharp melting peak at about 246±2° C. characteristic of crystalline form of compound of formula 1. This melting peak was absent in the DSC of blend of capsule of Example IV both before storage (FIG. 8) and after it was stored at 40° C. and 75% relative humidity for 6 months (FIG. 9). This demonstrated that the compound of formula I remained in amorphous state on storage throughout its shelf life, i.e. it was physically stable upon storage.

The invention claimed is:

1. A method of increasing stability of an oral, solid dosage form of a compound of Formula I, comprising providing an amorphous solid dispersion comprising the compound of Formula I and a fusible polymeric carrier, wherein the compound of Formula 1 is non-crystalline Formula I wherein the oral, solid dosage form contains less than 0.2% of N-oxide impurity by weight of the compound of Formula I following storage at 25° C. and 60% relative humidity for 24 months, wherein the N-oxide impurity is:

wherein a weight ratio of the fusible polymeric carrier to the compound of Formula I is about 7:1.

2. The method according to claim 1, wherein the oral, solid dosage form does not include a crystalline compound of Formula 1, as determined by a lack of diffraction peaks characteristic of a crystalline form of the compound of Formula I when measured using X-ray diffraction, or as determined by a lack of melting peaks of a crystalline form of the compound of Formula I when measured by differential scanning calorimetry.

3. The method according to claim 1, wherein the oral, solid dosage form further comprises less than 0.2% of stage V impurity by weight of the compound of Formula I following storage at 25° C. and 60% relative humidity for 24 months, wherein the stage V impurity is:

4. The method according to claim 1, wherein the oral, solid dosage form comprises less than 0.01 to 0.1% of N-oxide impurity by weight of the compound of Formula 1 in the oral, solid dosage form following storage at 25° C. and 60% relative humidity for 24 months.

5. The method according to claim 1, wherein the oral, solid dosage form is a powder.

6. The method according to claim 5, wherein all particles of the powder have a size less than 1000 microns.

7. The method according to claim 6, wherein all particles of the powder have a size of less than 750 microns.

8. The method according to claim 6, wherein all particles of the powder have a size below 425 microns.

9. The method according to claim 5, wherein at least 85% of particles in the powder have a size less than 250 microns.

10. The method according to claim 5, wherein at least 15% of particles in the powder have a size less than 75 microns.

11. The method according to claim 1, wherein the fusible polymeric carrier is polyvinyl caprolactam-polyvinyl acetate-polyethylene glycol graft co-polymer.

12. The method according to claim 1, wherein the amorphous solid dispersion is in a pulverized form wherein all particles have a size less than 500 microns.

13. The method according to claim 1, wherein the oral, solid dosage form is a capsule filled with the amorphous solid dispersion and a pharmaceutically acceptable excipient.

14. The method according to claim 1, wherein the amorphous solid dispersion is prepared by a method comprising a step of melt extruding a mixture comprising the compound of Formula I and a fusible polymeric carrier.

15. The method according to claim 14, wherein the amorphous solid dispersion is free from excipients.

16. The method according to claim 1, wherein the oral, solid dosage form is a hard gelatin capsule filled with the amorphous solid dispersion, wherein the amorphous solid dispersion has been milled.

17. The method according to claim 1, wherein the amorphous solid dispersion has a bulk density of less than 0.7 g/ml.

18. The method according to claim 17, wherein the amorphous solid dispersion has a bulk density of less than 0.6 g/ml.

19. The method according to claim 18, wherein the amorphous solid dispersion has a bulk density of less than 0.4 g/ml.

20. The method according to claim 18, wherein the amorphous solid dispersion has a bulk density of from 0.52-0.56 g/ml.

21. The method according to claim 1, wherein the oral, solid dosage form is a tablet, filled capsule, sachet, or pouch.

22. The method according to claim 3, wherein the oral, solid dosage form is-comprises less than 0.01 to 0.1% of stage V impurity by weight of the compound of Formula 1 in the oral, solid dosage form, following storage at 25° C. and 60% relative humidity for 24 months.

\* \* \* \* \*